(12) United States Patent
Allen, IV

(10) Patent No.: US 10,595,928 B2
(45) Date of Patent: *Mar. 24, 2020

(54) COMBINATION UNILATERAL/BILATERAL JAWS ON A SURGICAL INSTRUMENT

(71) Applicant: COVIDIEN LP, Mansfield, MA (US)

(72) Inventor: James D. Allen, IV, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 1223 days.

This patent is subject to a terminal disclaimer.

(21) Appl. No.: 14/593,574

(22) Filed: Jan. 9, 2015

(65) Prior Publication Data

US 2015/0126999 A1     May 7, 2015

Related U.S. Application Data

(63) Continuation of application No. 12/981,771, filed on Dec. 30, 2010, now Pat. No. 8,936,614.

(51) Int. Cl.
| | |
|---|---|
| *A61B 17/29* | (2006.01) |
| *A61B 18/14* | (2006.01) |
| *A61B 18/08* | (2006.01) |
| *A61B 17/00* | (2006.01) |

(52) U.S. Cl.
CPC .......... *A61B 18/1445* (2013.01); *A61B 17/29* (2013.01); *A61B 18/08* (2013.01); *A61B 2017/00398* (2013.01); *A61B 2017/2927* (2013.01); *A61B 2017/2936* (2013.01); *A61B 2017/2938* (2013.01); *A61B 2017/2946* (2013.01)

(58) Field of Classification Search
CPC ..... A61B 18/1445; A61B 18/08; A61B 17/29; A61B 2017/2927; A61B 2017/00398; A61B 2017/2938; A61B 2017/2936; A61B 2017/2946; A61B 18/1447; A61B 2018/145

See application file for complete search history.

(56) References Cited

U.S. PATENT DOCUMENTS

| | | |
|---|---|---|
| 2,028,635 A | 1/1936 | Wappler |
| 4,763,669 A | 8/1988 | Jaeger |
| 5,209,747 A | 5/1993 | Knoepfler |

(Continued)

*Primary Examiner* — Erich G Herbermann
(74) *Attorney, Agent, or Firm* — Carter, DeLuca & Farrell LLP

(57) ABSTRACT

A surgical instrument includes a housing supporting first and second actuators thereon, and an elongated shaft extending distally from the housing. First and second drive members extend through the elongated shaft to operatively couple respective actuators to respective jaw members such that independent manipulation of one of the actuators may induce pivotal movement of an individual jaw member. A locking member is operatively associated with the first and second drive members, and is selectively movable between locked and unlocked positions. When the locking member is in the locked position, the first and second drive members are coupled to one another and move concurrently to drive the jaw members in a bilateral manner. When the locking member is in the unlocked position, the drive members are decoupled from one another and move independently to permit operation of the instrument in a unilateral manner.

17 Claims, 9 Drawing Sheets

(56) References Cited

U.S. PATENT DOCUMENTS

| | | | | |
|---|---|---|---|---|
| 5,275,614 A | * | 1/1994 | Haber | A61B 17/0469 606/139 |
| 5,282,826 A | * | 2/1994 | Quadri | A61B 17/29 606/207 |
| 5,350,391 A | | 9/1994 | Iacovelli | |
| 5,456,684 A | * | 10/1995 | Schmidt | A61B 17/29 604/35 |
| 5,618,294 A | | 4/1997 | Aust et al. | |
| 5,700,276 A | | 12/1997 | Benecke | |
| 5,728,110 A | | 3/1998 | Vidal et al. | |
| 5,817,119 A | | 10/1998 | Klieman et al. | |
| 5,827,323 A | | 10/1998 | Klieman et al. | |
| 6,228,097 B1 | | 5/2001 | Levinson et al. | |
| 6,299,625 B1 | * | 10/2001 | Bacher | A61B 17/2909 606/167 |
| 6,506,208 B2 | | 1/2003 | Hunt et al. | |
| 6,592,572 B1 | | 7/2003 | Suzuta | |
| 6,673,092 B1 | * | 1/2004 | Bacher | A61B 17/2909 606/205 |
| 6,682,544 B2 | | 1/2004 | Mastri et al. | |
| 7,083,620 B2 | | 8/2006 | Jahns et al. | |
| 7,207,990 B2 | | 4/2007 | Lands et al. | |
| 7,487,780 B2 | | 2/2009 | Hooven | |
| 7,540,872 B2 | | 6/2009 | Schechter et al. | |
| 7,799,028 B2 | | 9/2010 | Schechter et al. | |
| 8,936,614 B2 | | 1/2015 | Allen, IV | |
| 2006/0190035 A1 | * | 8/2006 | Hushka | A61B 17/2909 606/205 |
| 2010/0016852 A1 | * | 1/2010 | Manzo | A61B 18/1445 606/46 |
| 2010/0042142 A1 | | 2/2010 | Cunningham | |
| 2011/0060376 A1 | * | 3/2011 | Li | A61B 17/8866 606/86 R |
| 2011/0106078 A1 | | 5/2011 | Mueller | |

* cited by examiner

COMBINATION UNILATERAL/BILATERAL JAWS ON A SURGICAL INSTRUMENT

CROSS REFERENCE TO RELATED APPLICATION

The present application is a continuation application of U.S. patent application Ser. No. 12/981,771, filed on Dec. 30, 2010, the entire contents of which are incorporated herein by reference.

BACKGROUND

1. Technical Field

The present disclosure relates to an apparatus for surgically treating tissue. In particular, the disclosure relates to a mechanism for orienting and operating a pair of jaw members by selectively inducing either independent or concurrent motion of the jaw members.

2. Background of Related Art

Instruments such as electrosurgical forceps are commonly used in open and endoscopic surgical procedures to coagulate, cauterize and seal tissue. Such forceps typically include a pair of jaw members that can be controlled by a surgeon to grasp targeted tissue, such as, e.g., a blood vessel. The jaw members may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaw members. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

Endoscopic forceps are typically provided with a pair of jaw members pivotally coupled to a distal end of an elongated shaft about a pivot axis. Often the jaw members may be induced to pivot between open and closed configurations in one of two manners. Some forceps are configured for unilateral jaw motion, wherein one jaw remains stationary relative to the distal end of the elongated shaft while the other jaw member pivots to open and close the jaws. Other forceps are configured for bilateral jaw motion, wherein both of the jaw members move relative to the distal end of the elongated shaft. A surgeon may have a preference for one of these modes of jaw motion over the other, and some surgical procedures may be more conveniently accomplished with one mode than the other.

Also, a surgeon may be inclined to articulate or orient the jaw members relative to the distal end of the elongated shaft. Articulation of the jaw members may be accomplished by pivoting the jaw members about the same pivot axis that the jaw members pivot about to move between the open and closed configurations. In this manner, the jaw members may be appropriately oriented to engage tissue, and may also be aligned with the elongated shaft to facilitate insertion or withdrawal of the jaw members from a surgical site. It may be advantageous to provide a surgical instrument that permits articulation of the jaw members, while providing selectivity between unilateral and bilateral jaw motion.

SUMMARY

The present disclosure describes a surgical instrument including a housing supporting first and second actuators. An elongated shaft extends distally from the housing and defines a longitudinal axis. First and second jaw members are pivotally coupled to a distal end of the elongated shaft about a pivot axis, and first and second drive members extend through the elongated shaft. The first drive member is operatively coupled between the first actuator and the first jaw member such that manipulation of the first actuator induces pivotal movement of the first jaw member about the pivot axis. Similarly, the second drive member is operatively coupled between the second actuator and the second jaw member such that manipulation of the second actuator induces pivotal movement of the second jaw member about the pivot axis. A locking member is operatively associated with the first and second drive members. The locking member is selectively movable between a locked position wherein the first and second drive members are coupled to one another and move concurrently to drive the jaw members in a bilateral manner, and an unlocked position wherein the first and second drive members are decoupled from one another and move independently to permit operation of the instrument in a unilateral manner.

The first and second drive members may be coupled to a respective drive pin, and each of the respective drive pins may be engaged with a cam slot defined in a respective jaw member. The cam slots may define a generally curvilinear path through the respective jaw member, and the cam slots may be disposed either proximally or distally with respect to the pivot axis.

The locking member may include a peg coupled to the first drive member, and the second drive member may include a plurality of holes for receiving the peg when the locking member is moved to the locked configuration. At least one of the first and second drive members may be operatively associated with an immobilization member that is operable to selectively impede motion of the drive member with respect to the housing. The immobilization member may include a peg receivable in the plurality of holes in the second drive member to impede motion of the second drive member with respect to the housing.

The first and second jaw members may be movable between an open configuration wherein the jaw members are substantially spaced relative to one another, and a neutral closed configuration wherein the first and second jaw members are closer together and generally aligned with the longitudinal axis. The first and second jaw members may also be movable between the open configuration and an offset closed configuration wherein the jaw members are closer together and obliquely disposed with respect the longitudinal axis. At least one of the first and second jaw members may include an electrode coupled to a source of electrosurgical energy.

According to another aspect of the disclosure, a surgical instrument includes a housing supporting at least one actuator thereon. An elongated shaft extends distally from the housing, and first and second jaw members are pivotally coupled to a distal end of the elongated shaft about a pivot axis. First and second drive members extend through the elongated shaft. The first drive member is operatively coupled between the at least one actuator and the first jaw member such that manipulation of the at least one actuator induces pivotal movement of the first jaw member about the pivot axis. The second drive member is operatively coupled between the at least one actuator and the second jaw member such that manipulation of the second actuator induces pivotal movement of the second jaw member about the pivot axis. An immobilization member is operatively associated with the second drive member. The immobilization member is movable between a locked position wherein motion of the second drive member is impeded such that manipulation of the at least one actuator induces unilateral jaw motion, and an unlocked position wherein motion of the second drive member is permitted such that manipulation of the at least one actuator induces bilateral jaw motion.

The at least one actuator may include a movable handle pivotally supported by the housing. The movable handle may be pivotable in a proximal direction to induce longitudinal translation of the first drive member in a distal direction. The first jaw member may be coupled to the first drive member by a drive pin extending into a cam slot defined in the first jaw member, and the cam slot may be disposed distally with respect to the pivot axis. The longitudinal translation of the first drive member in the distal direction may induce pivotal movement of the first jaw member about the pivot axis in a direction toward the second jaw member.

The first and second drive member may also be operatively coupled to independent first and second motors. Each of the first and second drive members include a generally flat surface disposed adjacent the generally flat surface of the other of the drive members.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
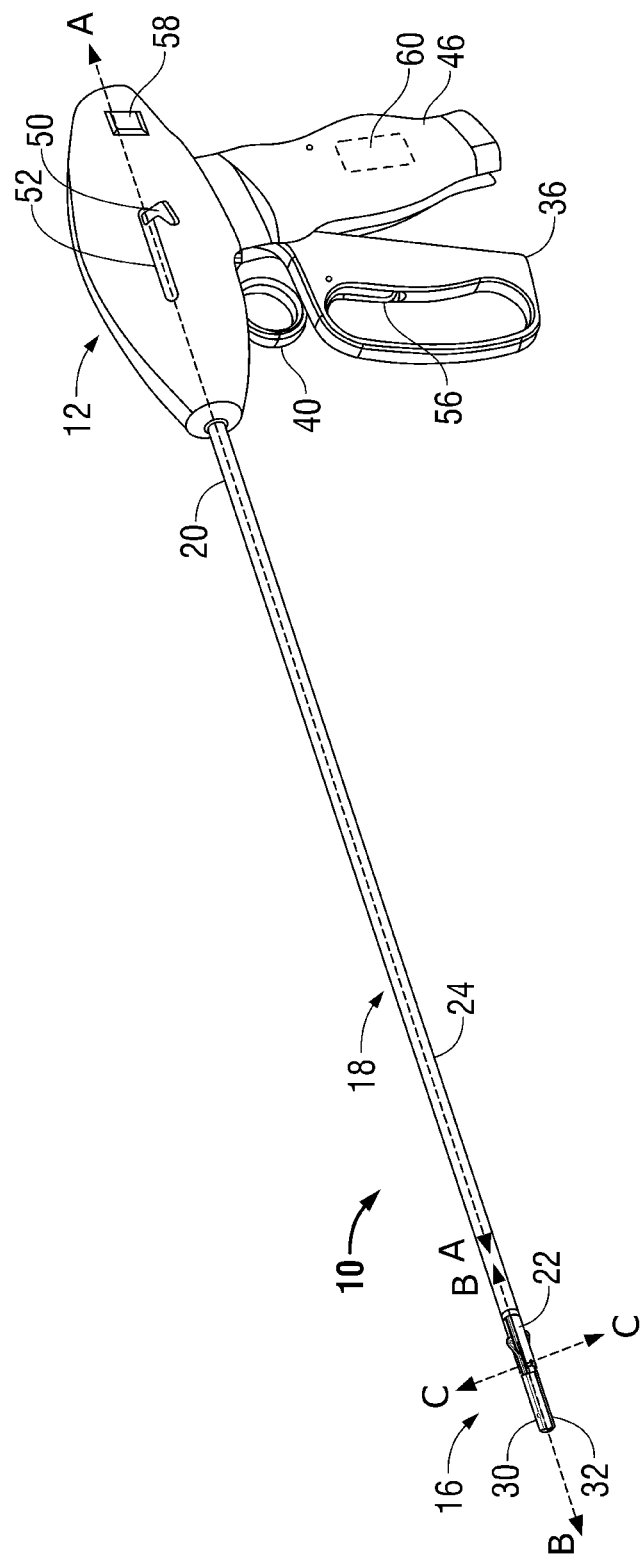
FIG. 1 is a perspective view of a surgical instrument in accordance with an embodiment of the present disclosure.

Referring initially to FIG. 1, an embodiment of an electrosurgical instrument 10 is depicted in a neutral configuration. The instrument 10 includes a proximal housing 12 that remotely supports an end effector 16 through an elongated shaft 18. This configuration is typically associated with instruments for use in endoscopic surgical procedures, although various aspects of the present disclosure may be practiced in connection with traditional open procedures as well.

Elongated shaft 18 includes a proximal end 20 adjacent to the housing 12, and a distal end 22 supporting the end effector 16. The elongated shaft 18 includes an outer tubular member 24 that houses various internal components of the instrument 10 (see, e.g., FIG. 2), and extends a sufficient distance to permit the end effector 16 to be positioned through a cannula (not shown). A longitudinal axis A-A is defined through the elongated shaft 18, and the end effector 16 defines an end effector axis B-B. The end effector 16 and the end effector axis B-B are pivotable about a pivot axis C-C defined through the distal end 22 of the elongated shaft 18. Thus, the end effector 16 may be aligned with the longitudinal axis A-A to facilitate insertion of the end effector 16 through the cannula, and thereafter the end effector 16 may be moved or articulated to orient the end effector 16 relative to a surgical site within the body of a patient.

The end effector 16 includes an upper jaw member 30 and a lower jaw member 32. The jaw members 30, 32 are operable from the housing 12 to move between various open configurations (see, e.g., FIGS. 4B, 5A and 6A) to receive tissue, and various closed configurations (see, e.g., FIGS. 4A, 5B and 6B) to clamp the tissue and impart an appropriate clamping force thereto. When the end effector 16 is in an open configuration, a distal portion of each of the jaw members 30, 32 is spaced from the distal portion of the other of the jaw members 30, 32. When the end effector 16 is in a closed configuration, the distal portions of the jaw members 30, 32 are closer together. To move between the open and closed configurations, both of the jaw members 30, 32 are pivotable about the pivot axis C-C.

As described in greater detail below, the end effector 16 is configured for both unilateral and bilateral jaw motion. Unilateral jaw motion is characterized in that only one or the other of the jaw members 30, 32 moves relative to the end effector axis B-B when the end effector 16 is induced to move between open and closed configurations. In contrast, bilateral jaw motion is characterized in that both jaw members 30 and 32 move relative to the end effector axis B-B when the end effector 16 is induced to move between the open and closed configurations.

Figure 2:
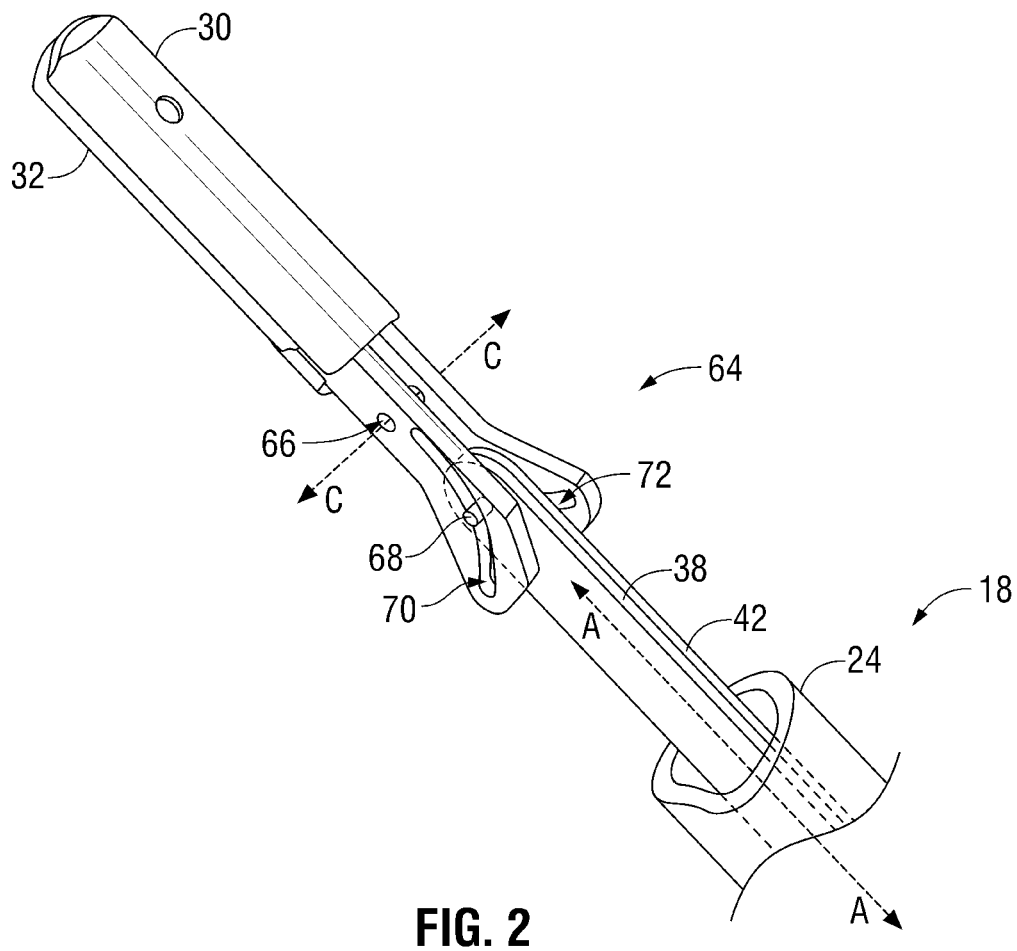
FIG. 2 is an enlarged perspective view of a distal end of the instrument depicting a drive mechanism including first and second drive shafts for moving respective upper and lower jaw members.

The housing 12 supports various actuators that are responsive to manipulation by an operator to induce these and other movements of the end effector 16. These actuators include a movable handle 36 and a drive ring 40. The movable handle 36 is operatively coupled to the upper jaw member 30 by a first drive member or shaft 38 (FIG. 2), and the drive ring 40 is operatively coupled to the lower jaw member 32 through an independent, second drive member or shaft 42 (FIG. 2). The movable handle 36 may be approximated and separated relative to a stationary handle 46 to induce motion of the upper jaw member 30 relative to the end effector axis B-B. Similarly, the drive ring 40 may be translated longitudinally in proximal and distal directions to induce movement of the lower jaw member 32 relative to the end effector axis B-B. A coupling member 50 protrudes from a slot 52 in the housing 12, and is operable to selectively permit concurrent and independent motion of the jaw members 30, 32. As described in greater detail below with reference to FIGS. 7A and 7B, the coupling member 50 serves to couple the drive members 38, 42 to one another for concurrent or bilateral motion of the jaw members, and decouple the drive members 38, 42 from one another for independent or unilateral motion of the jaw members 30, 32. An immobilization member 90 (FIG. 7A) protrudes from an opposite side of the housing 12, and is operable to selectively stabilize the position of the lower jaw member 32 to facilitate unilateral jaw motion.

An additional actuator supported on the housing 12 is a locking trigger 56. The locking trigger 56 is operable to selectively maintain the end effector 16 in a closed configuration by maintaining the relative positions of the upper and lower jaw members 30, 32. When the jaw members 30, 32 are locked in the closed configuration about tissue, the surgeon may initiate the delivery of electrosurgical energy to the jaw members 30, 32 by manipulating a push button 58 provided on the housing 12. In alternate embodiments, the delivery of electrosurgical energy may be initiated with a footswitch (not shown) or other external actuators. Push button 58 is in electrical communication with a source of electrosurgical energy such as electrosurgical generator 60. The electrosurgical generator 60 serves to produce electrosurgical energy and also to control and monitor the delivery of the electrosurgical energy. Various types of electrosurgical generators 60, such as those generators provided by Covidien—Energy-based Devices, of Boulder, Colo., may be suitable for this purpose. Electrosurgical generator 60 may be housed within the stationary handle 46 as depicted schematically in FIG. 1, or may alternatively be electrically and mechanically coupled to the instrument 10 by a cable (not shown). The electrosurgical generator 60 is in electrical communication with an electrode 80 (FIG. 3) supported on a tissue contacting surface of at least one of the jaw members 30, 32.

Referring now to FIG. 2, a drive mechanism 64 is provided for selectively inducing both unilateral and bilateral motion of the jaw members 30, 32. The jaw members 30, 32 are pivotally supported at a distal end of the outer tubular member 24 about the pivot axis C-C. A pivot pin or axle (not shown) may be provided that extends into the outer tubular member 24 through a pivot bore 66 that extends laterally through each of the jaw members 30, 32.

To induce pivotal motion of the jaw members 30, 32 the drive mechanism 64 includes first and second drive shafts 38, 42. The drive shafts 38, 42 are constructed as bar members having generally flat surfaces on each lateral side. This configuration provides the drive shafts 38, 42 with sufficient strength while permitting the drive mechanism 64 to maintain a limited spatial cross section. The drive shafts 38, 42 are supported adjacent one another in a manner that permits selective independent and concurrent longitudinal motion of the drive shafts 38, 42 through the outer tubular member 24. A cam pin 68 is provided at a distal end of each of the drive shafts 38, 42 that protrudes laterally outward into a respective cam slot 70, 72 defined in a respective jaw member 30, 32. The cam slots 70, 72 define a generally curvilinear path through the respective jaw member 30, 32, and thus, longitudinal motion of the drive shafts 38, 42 drives the cam pins 68 through the cam slots 70, 72 to induce pivotal motion of the jaw members 30, 32 about the pivot axis C-C. A proximal end of each of the drive shafts 38, 42 is coupled to a respective actuator as described in greater detail below with reference to FIG. 8.

Figure 3:
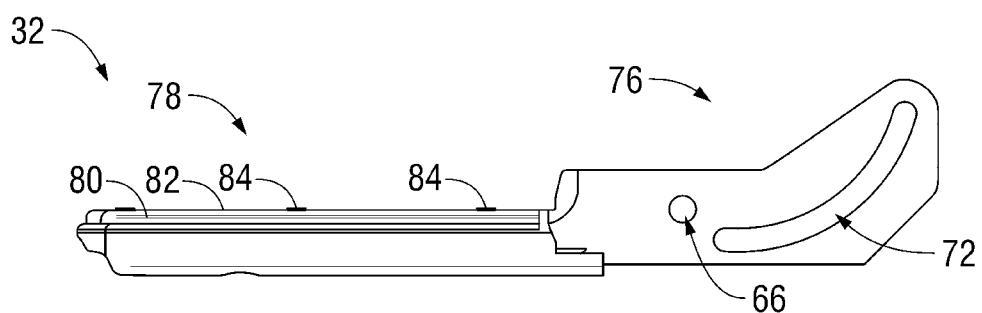
FIG. 3 is a side view of the lower jaw member.

Referring now to FIG. 3, the lower jaw member 32 includes a proximal drive flange 76 and a distal clamping portion 78. The pivot bore 66 and the cam slot 72 are defined through the proximal drive flange 76, and serve to drive pivotal motion of the jaw member 32 as described above. The distal clamping portion 78 is provided to surgically engage tissue.

The distal clamping portion 78 includes an electrode 80 having an electrically conductive tissue contacting surface 82 and a plurality of electrically isolative stop members 84 protruding therefrom. The tissue contacting surface 82 of the electrode 80 is oriented to provide a clamping force to tissue captured between the tissue contacting surface 82 of the lower jaw member 32 and the upper jaw member 30 (FIG. 2). A clamping pressure within the range of about 3 kg/cm$^2$ to about 16 kg/cm$^2$ may be appropriate for sealing tissue. The stop members 84 define a separation or gap distance between the upper and lower jaw members 30, 32 when the jaw members 30, 32 are in a closed configuration. An appropriate gap distance for generating an effective tissue seal may be between about 0.001 inches and about 0.006 inches. A gap distance between about 0.002 inches and about 0.003 inches may be preferred in some instances. The electrosurgical generator 60 (FIG. 1) is coupled to the electrode 80 through a lead wire (not shown) or other mechanism such that electrosurgical energy may be delivered to tissue through the tissue contacting surface 82.

The upper jaw member 30 may be similarly configured with an electrode that is coupled to an opposite terminal of the electrosurgical generator 60 such that bipolar electrosurgical energy may be delivered to the tissue. In alternative embodiments, monopolar energy may be delivered through the electrode 80 on the lower jaw member 32, and a return pad (not shown) may be positioned beneath a patient to provide a return path to the electrosurgical generator 60.

Figure 4A:
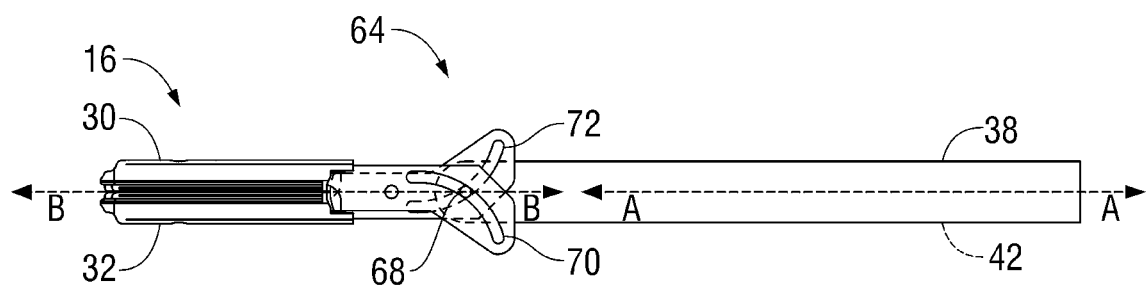
FIG. 4A is a side view of the drive mechanism depicting the jaw members in a neutral, closed configuration.

Referring now to FIG. 4A, the drive mechanism 64 is arranged such that the jaw members 32, 34 establish a neutral, closed configuration. In the neutral, closed configuration, the end effector axis B-B is aligned with the longitudinal axis A-A, and the jaw members 30, 32 are positioned adjacent one another. The jaw members 30, 32 may be selectively moved to the neutral, closed configuration to facilitate insertion of the end effector 16 through a narrow cannula (not shown) since the neutral, closed configuration represents a minimum diameter of the end effector 16. The drive shafts 38, 42 are in general longitudinal alignment with one another, and longitudinally positioned such that the cam pins 68 are centrally arranged within the cam slots 70, 72.

Figure 4B:
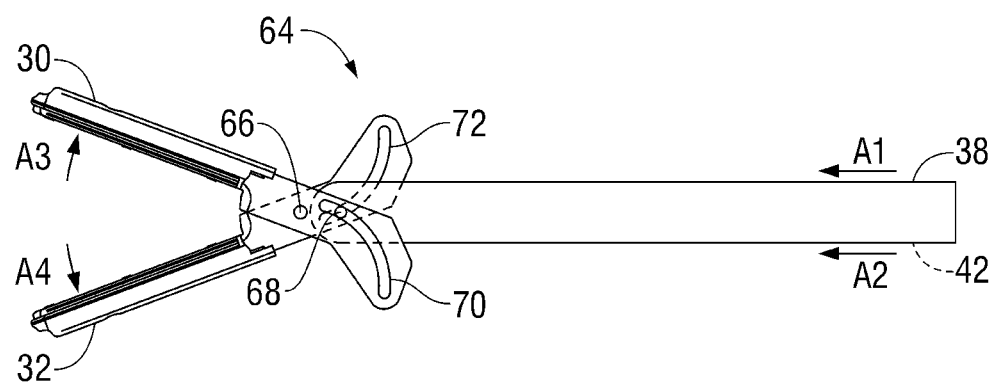
FIG. 4B is a side view of the drive mechanism depicting the jaw members moved to a bilateral open configuration.

From the neutral, closed configuration, the drive mechanism 64 may be manipulated to move the jaw members 30, 32 concurrently to the bilateral, open position depicted in FIG. 4B. Both of the drive members 38, 42 are concurrently driven distally in the direction of arrows A1 and A2 to advance the cam pins 68 to a distal position within the cam slots 70, 72. This induces bilateral pivotal motion of the jaw members 30, 32 about the pivot bores 66 in the direction of arrows A3 and A4. The bilateral, open configuration represents a relatively large separation between the jaw members 30, 32 such that tissue may readily be received therebetween. The bilateral, open configuration of FIG. 4B may alternatively be achieved by sequential, unilateral movements of the jaw members 30, 32.

Figure 5A:
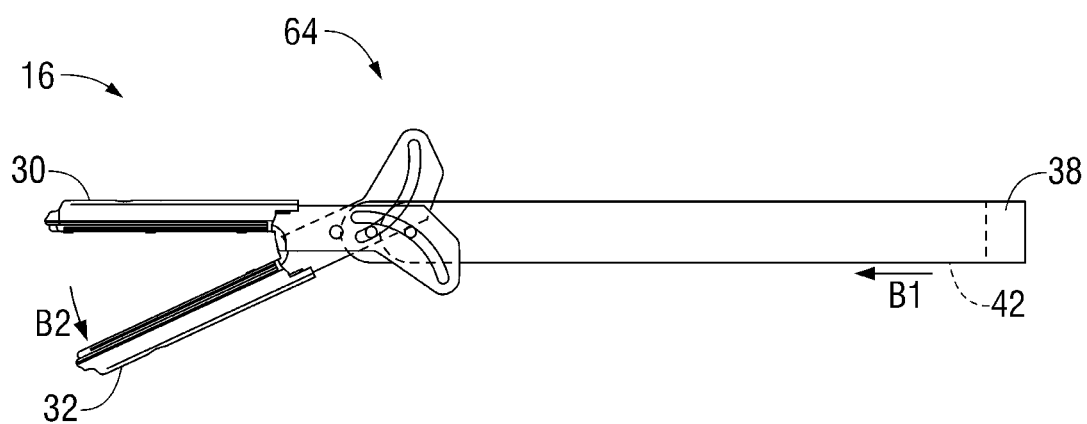
FIG. 5A is a side view of the drive mechanism depicting the jaw members moved to a uni-lateral, down, open configuration.

Referring now to FIG. 5A, the drive mechanism 64 is arranged such that the jaw members 32, 34 establish a unilateral, down and open configuration. To achieve the unilateral, down and open configuration from the neutral, closed configuration depicted in FIG. 4A, the second drive shaft 42 is advanced distally in the direction of arrow B1 while the longitudinal position of the first drive shaft 38 is maintained. Since the longitudinal position of the first drive shaft 38 is maintained, the pivotal position of the upper jaw member 30 is maintained. The movement of the second drive shaft 42 induces the lower jaw member 32 to move unilaterally in the direction of arrow B2 such that the end effector 16 is arranged in an open configuration. From the unilateral, down and open configuration, the drive mechanism 64 may be manipulated to achieve the unilateral down closed position depicted in FIG. 5B. The first drive shaft 38 is drawn proximally in the direction of arrow B3 while the longitudinal position of the second drive shaft 42 is maintained. This induces unilateral, pivotal motion of the upper jaw member 30 toward the lower jaw member 32 in the direction of arrow B4.

Figure 5B:
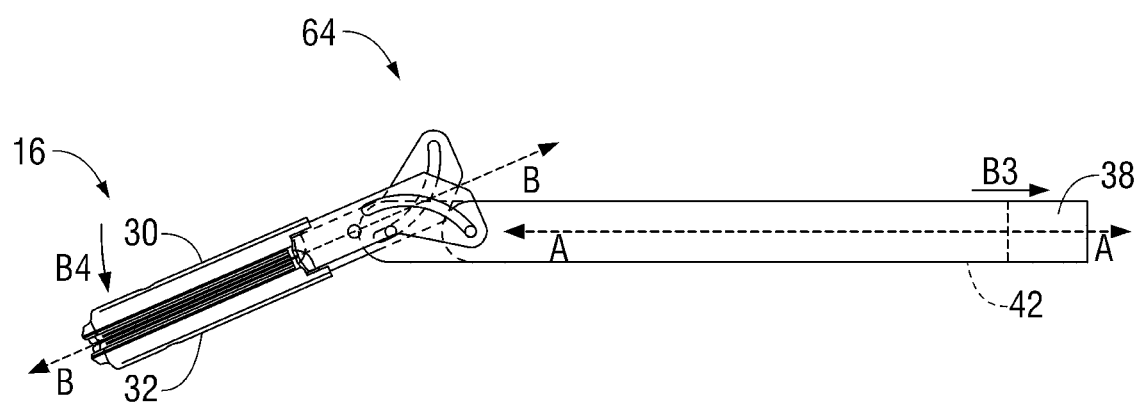
FIG. 5B is a side view of the drive mechanism depicting the jaw members moved to a uni-lateral, down, closed configuration.

In the unilateral, down and closed configuration of FIG. 5B, the end effector axis B-B is offset or articulated in a downwardly sloping direction with respect to the longitudinal axis A-A. This articulation capability of end effector 16 facilitates the grasping of tissue by enabling adjustments to the orientation of the end effector 16. A unilateral, upward and closed configuration (not shown) is also contemplated in which the jaw members 30, 32 are moved such that the end effector axis B-B slopes upward with respect to the longitudinal axis A-A. To achieve the unilateral, upward and closed configuration, the drive mechanism 64 may be manipulated in an opposite manner than the manner in which the drive mechanism 64 is manipulated to achieve the unilateral, down and closed configuration as described above.

Figure 6A:
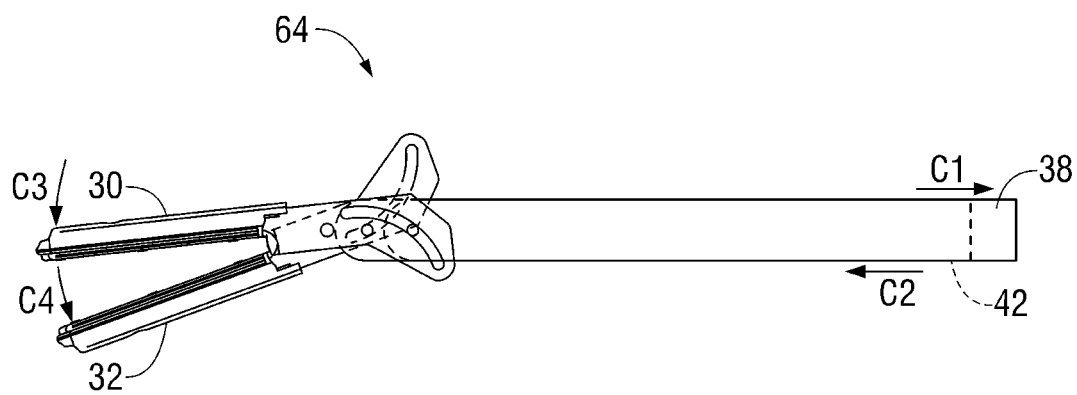
FIG. 6A is a side view of the drive mechanism depicting the jaw members moved to a bilateral, offset, down, open configuration.
Figure 6B:
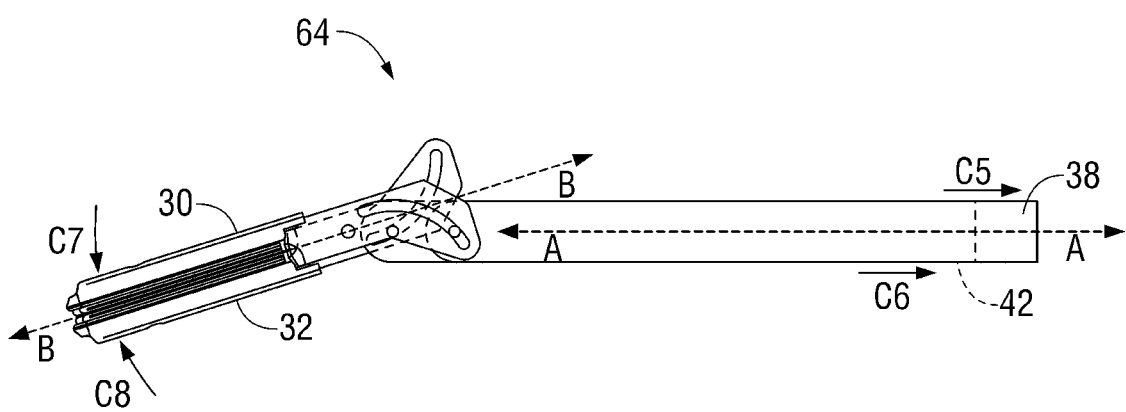
FIG. 6B is a side view of the drive mechanism depicting the jaw members moved to bilateral, offset, down, closed configuration.

Referring now to FIG. 6A, the drive mechanism 64 is arranged such that the jaw members 32, 34 establish a bilateral, down and open configuration. To achieve the bilateral, down and open configuration from the neutral, closed configuration depicted in FIG. 4A, the first drive shaft 38 may be drawn proximally in the direction of arrow C1 while the second drive shaft 42 is advanced distally in the direction of arrow C2 to induce both of the jaw members 30, 32 to pivot downward in the direction of arrows C3 and C4. From the bilateral, down and open configuration, the drive mechanism 64 may be manipulated to achieve the bilateral, down and closed position depicted in FIG. 6B. The first and second drive shafts 38 and 42 are concurrently drawn proximally in the direction of arrows C5 and C6 to induce bilateral, pivotal motion of the upper and lower jaw members in the direction of arrows C7 and C8.

Figure 7A:
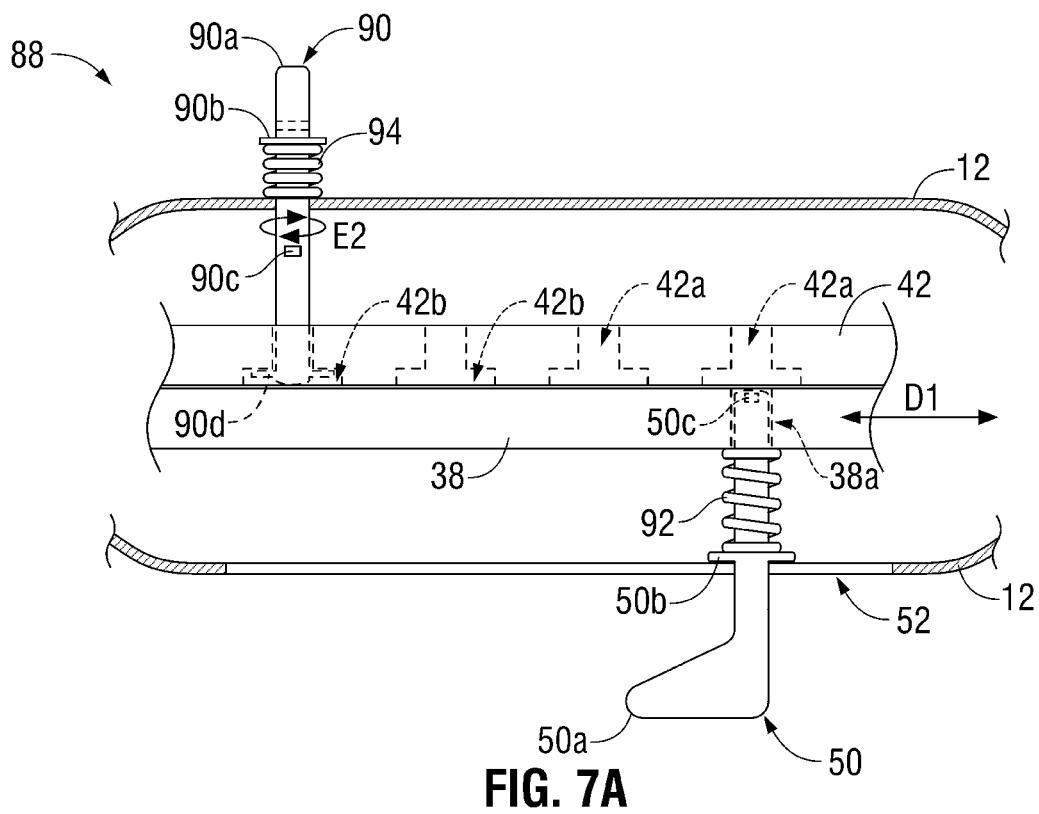
FIG. 7A is a schematic view of a proximal portion of the drive mechanism depicting the first drive shaft in an immobilized configuration, and the second drive shaft uncoupled from the first drive shaft for permitting independent motion of the second drive shaft.
Figure 7B:
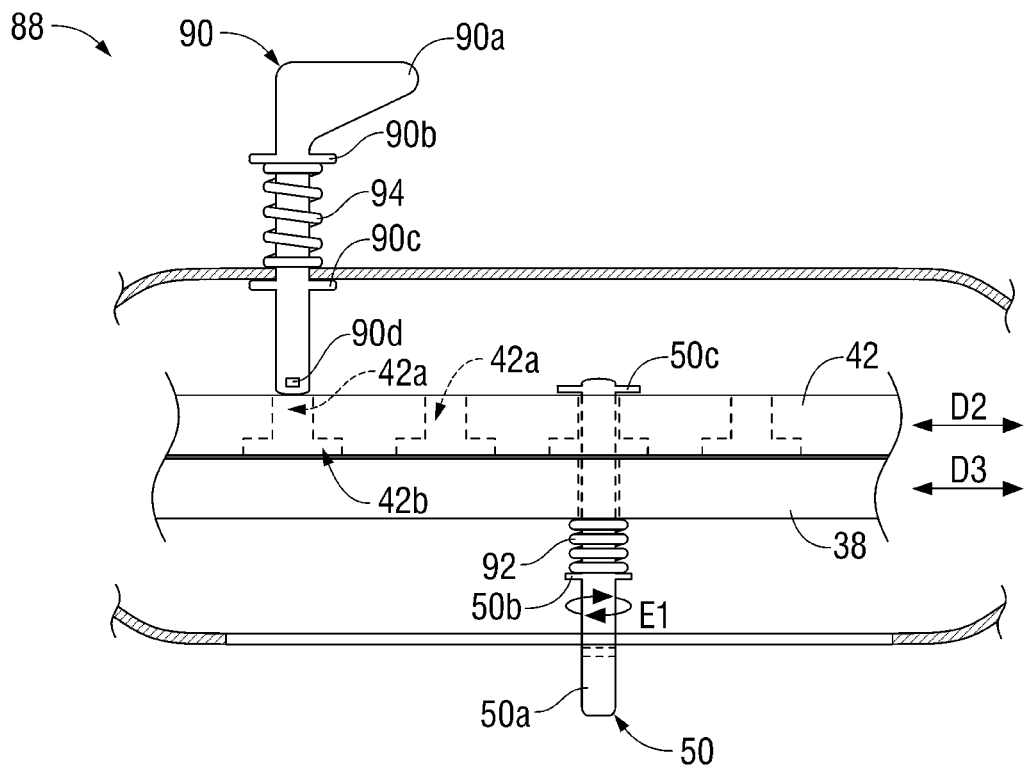
FIG. 7B is a schematic view of the proximal portion of the drive mechanism depicting the first drive shaft in a mobile configuration, and the second drive shaft coupled to the first drive shaft for permitting concurrent motion of the first and second drive shafts.

Referring now to FIGS. 7A and 7B, a locking mechanism 88 is provided for selectively configuring the drive members 38, 42 for a particular style of motion, e.g., unilateral or bilateral motion. The locking mechanism 88 includes the coupling member 50 and the immobilization member 90 described above with reference to FIG. 1. The coupling member 50 is operable to selectively couple the first and second drive shafts 38, 42 to one another to facilitate concurrent or bilateral motion of the jaw members 30, 32 (as described above with reference to FIG. 4B, for example). Similarly, the coupling member 50 is operable to selectively decouple the first and second drive shafts 38, 42 from one another to facilitate independent or unilateral motion of the jaw members 30, 32 (as described above with reference to FIG. 5B, for example). The immobilization member 90 is operable to selectively immobilize or prohibit longitudinal motion of the second drive shaft 42 relative to the housing 12. Maintaining the longitudinal position of the second drive member 42 facilitates independent longitudinal motion of the first drive member 38.

The coupling member 50 protrudes from the slot 52 defined on a lateral side of the housing 12. Thus, a handle portion 50a of the coupling member 50 may be manipulated from outside the housing 12. On the interior of the housing 12, the coupling member 50 includes a flange portion 50b that is engaged by a biasing member such as compression spring 92. The compression spring 92 is positioned between the first drive shaft 38 and flange portion 50b such that the coupling member 50 is biased to an unlocked position wherein the coupling member 50 does not extend into the second drive shaft 42, and wherein the flange portion 50b is disposed adjacent an interior wall of the housing 12 as depicted in FIG. 7A. When the coupling member 50 is in the unlocked position, a pair of locking wings 50c on an and end of the locking member 50 are disposed within an oblong slot 38a defined in the first drive shaft 38, and the first drive shaft 38 is decoupled from the second drive shaft 42. Thus, the first drive shaft 38 is free to move longitudinally in the direction of arrows D1 independently of the second drive shaft 42.

A user may drive the first drive member 38 longitudinally to align the coupling member 50 with one of a plurality of oblong holes or slots 42a (see also FIG. 8) extending through the second drive shaft 42. The slots 42a may be longitudinally spaced from another in regular intervals or in strategic locations to correspond to particular locations in which a transition between unilateral and bilateral jaw motion is anticipated. To couple the first and second drive shafts 38, 42 to one another, the coupling member 50 may be moved to a locked position as depicted in FIG. 7B. The coupling member may be pressed against the bias of compression spring 92 until the locking wings 50c emerge from slots 42a in the second drive shaft 42. The handle portion 50a may then be rotated in the direction of arrows E1 to rotate the locking wings 50c to an orientation wherein the locking wings 50c engage the second drive shaft 42 and prevent the bias of the spring 92 from withdrawing the coupling member 50 from slots 42a. When the coupling member 50 is in the locked position, the first and second drive shafts 38, 42 are coupled to one another and may be translated concurrently in the direction of arrows D2 and D3 to facilitate bilateral jaw motion.

The immobilization member 90 protrudes from an opposite lateral side of the housing 12 to selectively engage the second drive shaft 42. The immobilization member 90 includes a handle portion 90a, an exterior flange 90b, an interior flange 90c and a pair of locking wings 90d. A compression spring 94 is disposed between the exterior flange 90b and an outer wall of the housing 12 to bias the immobilization member 90 outward with respect to the housing 12. To move the immobilization member 90 to a locked configuration, the immobilization member 90 may be pressed against the bias of the spring 94 until the locking wings 90d encounter an undercut portion 42b of the oblong slots 42a defined in the second drive shaft 42. The handle portion 90a may then be rotated in the direction of arrows E2 to rotate the locking wings 90d to an orientation wherein the locking wings 90d engage the second drive shaft 42 and prevent the bias of the spring 94 from withdrawing the immobilization member 90 from slots 42a. When the immobilization member 90 is in the locked configuration depicted in FIG. 7A, longitudinal motion of the second drive shaft 42 with respect to the housing 12 is prohibited. By maintaining the longitudinal position of the second drive shaft 42, the pivotal position of the lower jaw member 32 (FIG. 5B) is likewise maintained. Thus, the first drive shaft 38 may be translated to move the upper jaw member 30 (FIG. 5B) in a unilateral manner. An additional immobilization member (not shown) may be provided to similarly immobilize or permit longitudinal motion of the first drive shaft 38.

Figure 8:
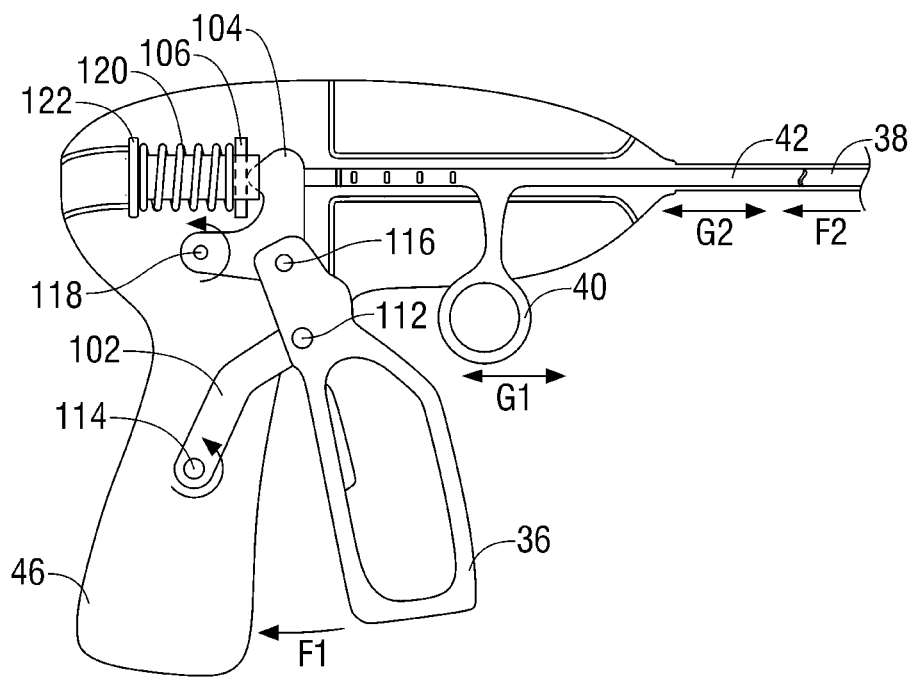
FIG. 8 is a side view of an actuation mechanism including actuators for selectively inducing the independent and concurrent motion of the first and second drive shafts.

Referring now to FIG. 8, the first and second drive shafts 38, 42 are operatively associated with the respective actuators including the movable handle 36 and the drive ring 40. The first drive shaft 38 is coupled to the movable handle 36 by a mechanical linkage including a pivotal link 102, a cam link 104, a drive plate 106, a compression spring 120 and a coupling 122. The pivotal link 102 is coupled to the movable handle 36 by a pivot pin 112, and is coupled to the stationary handle 46 by a pivot pin 114. Similarly, the cam link 104 is coupled to the movable handle by a pivot pin 116, and is coupled to the stationary handle 46 by a pivot pin 118. The drive plate 106 is engaged by the cam link 104 and the compression spring 120 on opposing sides thereof. The compression spring 120 also engages the coupling 122, which is fixedly coupled to the first drive shaft 38.

Longitudinal motion may be imparted to the first drive shaft 38 by approximating and separating the movable handle 36 with respect to the stationary handle 46. For example, the movable handle 36 may be pivoted toward the stationary handle 46 in the direction of arrow F1 to impart proximal longitudinal motion to the first drive shaft 38 in the direction of arrow F2. The movable handle 36 pivots generally about pivot pin 116, which induces a proximal pivotal motion (counter-clockwise as depicted in FIG. 8) to both the pivotal link 102 about pivot pin 114 and the cam link 104 about pivot pin 118. The proximal pivotal motion of the cam link 104 drives the drive plate 106, the compression spring 120 and the coupling 122 proximally. Since the coupling 122 is fixedly coupled to the first drive shaft 38, the first drive shaft 38 is correspondingly moved proximally in the direction of arrow F2. As described above with reference to FIG. 5B, for example, proximal longitudinal motion of the first drive shaft 38, in turn, induces pivotal motion of the upper jaw member 30 toward the lower jaw member 32. The inclusion of the compression spring 120 in the mechanical linkage facilitates control of the force transmitted to the first drive shaft 38, and thus facilitates control of a seal force generated between the jaw members 30, 32.

Longitudinal motion may be imparted to the second drive shaft 42 by sliding the drive ring 40 longitudinally. The second drive shaft 42 is directly coupled to the drive ring 40 such that longitudinal motion of the drive ring 40 in the direction of arrows G1 induces a corresponding longitudinal motion of the drive shaft 42 in the direction of arrows G2.

When the mechanisms described with reference to FIG. 8 (for imparting longitudinal motion to the first and second drive shafts 38, 42) are employed in conjunction with the locking mechanisms described above with reference to FIGS. 7A and 7B (for impeding or coupling the motion of the first and second drive shafts 38, 42), the various modes of motion of the upper and lower jaw members 30, 32 described with reference to FIGS. 4A through 6B may be achieved. These mechanisms are merely exemplary, and alternate mechanisms may be substituted for a particular purpose.

Figure 9:
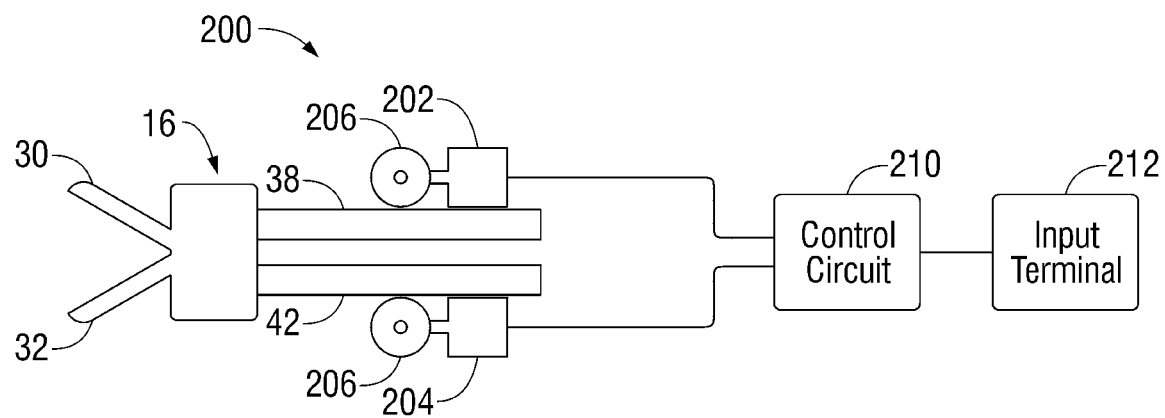
FIG. 9 is a schematic view of an alternate embodiment of actuation mechanism including an input terminal for selectively inducing independent and concurrent motion of a pair of motors, which are operatively associated with the first and second drive shafts.

For example, the motion of the first and second drive shafts 38, 42 may be controlled and powered by independent motors, servos, pneumatics, hydraulics, etc. As depicted in FIG. 9, an alternate drive mechanism 200 including a pair of motors 202, 204 may be employed for controlling and driving motion of the jaw members 30, 32 of end effector 16. The motors 202, 204 are operatively coupled to a respective drive shaft 38, 42 through a friction drive wheel 206. The drive wheels 206 may impart both proximal and distal longitudinal motion to the drive shafts 38, 42, as well as maintaining the longitudinal position of the drive shafts 38, 42. The motors 202, 204 receive electronic signals from a control circuit 210 that are representative of instructions input by a user at an input terminal 212. The drive mechanism 200 provides the capability to operate the motors 202, 204 simultaneously, and thus, impart concurrent motion of the drive members 38, 42 to induce bilateral motion of the jaw members 30, 32. The drive mechanism 200 also provides the capability to operate the motors 202, 204 independently to induce unilateral motion of the jaw members.

Figure 10:
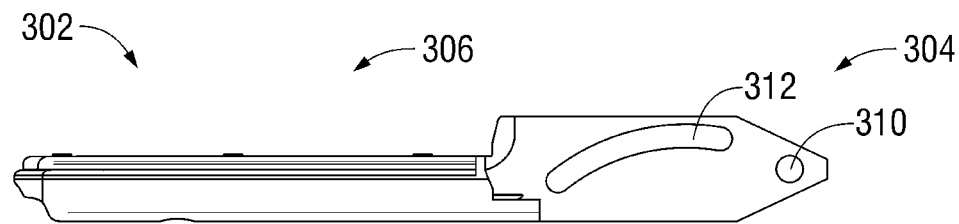
FIG. 10 is a side view of an alternate embodiment of a lower jaw member having a proximal flange defining a pivot axis and a cam slot arranged such that the pivot axis is proximally disposed with respect to the cam drive slot.

Referring now to FIG. 10, an alternate embodiment of a lower jaw member 302 includes a proximal drive flange 304 and a distal clamping portion 306. The distal clamping portion 306 may be similarly configured as the distal clamping portion 70 of the jaw member 32 described above with reference to FIG. 3. The proximal drive flange 304, however, differs from the proximal drive flange of jaw member 32 in that a pivot bore 310 is disposed proximally, rather than distally, of a cam slot 312.

The proximal position of the pivot bore 310 relative to the cam slot 312 affords greater spacing between the pivot bore 310 and the tissue contacting surfaces of the distal clamping portion 306 than would a distal position of the pivot bore 310. The spacing supplies the jaw member 302 with an increased moment arm, thus facilitating the application of an appropriate amount of pressure for generating a tissue seal. Also, the proximal position of the pivot bore 310 permits the jaw member 302 to pivot from a proximal-most portion of the drive flange 304. Thus, when jaw member 302 is pivotally coupled to an elongated shaft (not shown) the drive flange 304 will not protrude laterally from the elongated shaft. The reduced profile provided by the proximal position of the pivot hole 310 may facilitate insertion of the jaw member 302 into a surgical site through a cannula (not shown).

The lower jaw member 302 and a corresponding upper jaw member (not shown) may be incorporated into an instrument employing first and second drive shafts 38, 42 and a locking mechanism 88 (FIGS. 7A and 7B) to permit selective unilateral and bilateral jaw motion. However, since the longitudinal positions of the pivot bore 310 and cam slot 312 are reversed as compared to the jaw member 32 described above, the first and second drive shafts 38, 42 must also be configured to operate in reverse. A distal motion of the drive shafts 38, 42, rather than the proximal motion described above with reference to FIG. 6B, will induce jaw members configured as jaw member 302 to approximate and move toward a closed configuration.

Figure 11:
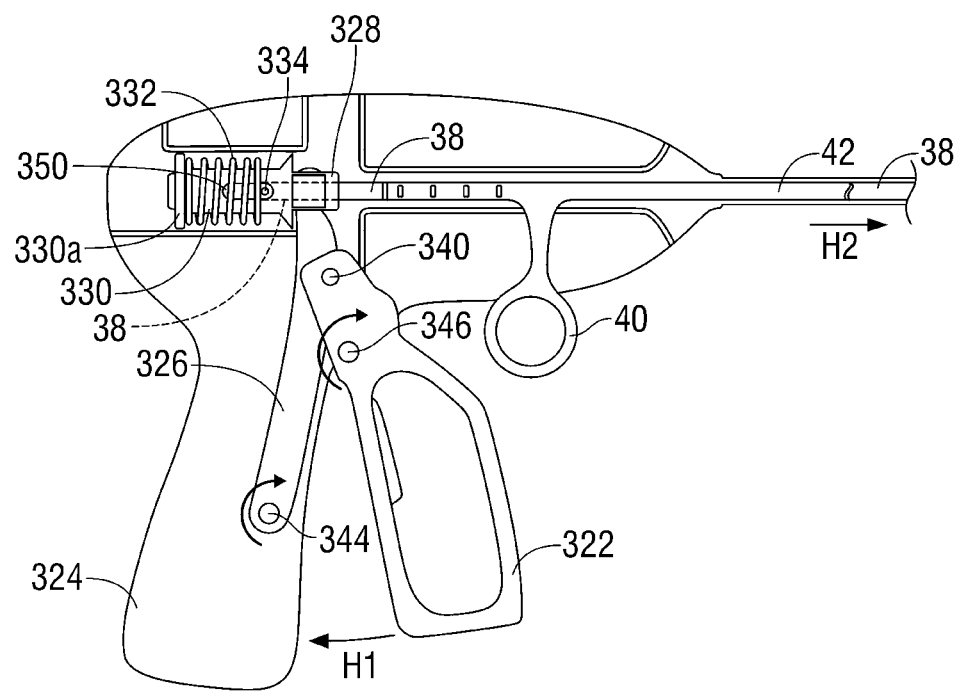
FIG. 11 is a side view of an actuation mechanism including actuators for selectively inducing independent and concurrent motion of a pair of jaw members configured as the jaw member depicted in FIG. 9.

As depicted in FIG. 11, a movable handle 322 is operatively coupled to the first drive shaft 38 such that approximation of the movable handle 322 toward a stationary handle 324 in the direction of arrow H1 induces a distal motion to drive shaft 38 in the direction of arrow H2. The first drive shaft 38 is coupled to the movable handle 322 by a mechanical linkage including a pivotal link 326, a cam plate 328, a barrel 330, a compression spring 332 and a coupling pin 334. The pivotal link 326 is coupled to the movable handle 322 by a pivot pin 340, and coupled to the stationary handle 324 by a pivot pin 344. The movable handle 322 is additionally coupled to the stationary handle 324 by a pivot pin 346. The cam plate 328 is coupled to the barrel 330 such that longitudinal motion imparted to the cam plate 328 is transmitted to the barrel 330. A flange 330a of the barrel 330 engages the compression spring 332 such that the spring 332 is confined between the flange 330a and the coupling pin 334. The coupling pin 334 is fixedly coupled to the proximal end of the drive shaft 38 such that longitudinal motion imparted to the coupling pin 334 is transmitted to the first drive shaft 38.

When the movable handle 322 is approximated toward the stationary handle 324, the movable handle 322 is induced to pivot generally (clockwise as depicted in FIG. 11) about the pivot pin 346. This motion drives the pivot pin 340 in a distal direction inducing pivotal link 326 to pivot distally (clockwise) about the pivot pin 344. The distal pivotal motion of the pivotal link 326 drives the cam plate 328 and the barrel 330 distally. The flange 330a of the barrel 330, in turn, drives the compression spring 332 distally against the coupling pin 334. The compression spring 332 supplies a distally directed force to the coupling pin 334 that is transmitted to the first drive shaft 38 to drive the first drive shaft 38 distally in the direction of arrow H2. A slot 350 is defined in the barrel 330. The slot 350 permits the coupling pin 334 to move independently of the barrel 330 as induced by the compression spring 332. Thus, the force applied to the first drive shaft 38, and the corresponding seal pressure generated by the jaw members 30, 32, may be regulated by the compression spring 332.

Thus, the movable handle 322 may be employed to control a jaw member configured similarly to jaw member 302. Since the drive ring 40 is directly coupled to the second drive shaft 42, the drive ring 40 may simply be translated longitudinally in a reverse direction to control a jaw member configured similarly to jaw member 302.

Figure 12:
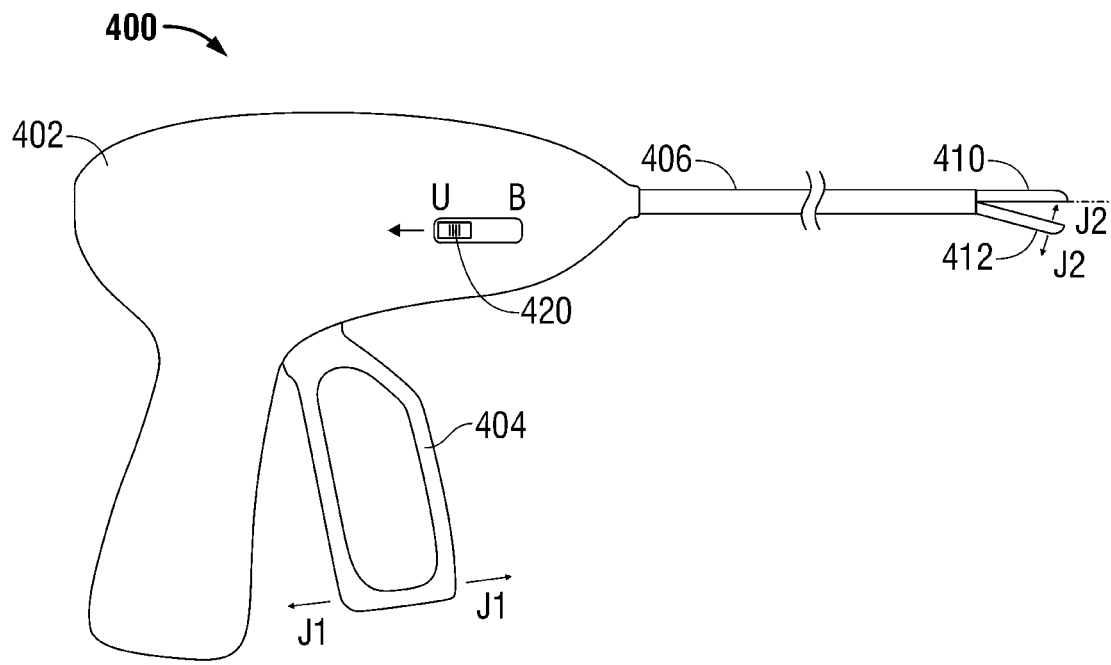
FIG. 12 is a side view of a surgical instrument in accordance with an alternate embodiment of the present disclosure arranged for operation in a unilateral mode.

Referring now to FIG. 12, an alternate embodiment of a surgical instrument 400 is arranged for operation in a unilateral mode. The instrument 400 includes a housing 402 supporting a movable handle 404. The movable handle 404 is supported for pivotal motion relative to the housing 402 in the direction of arrows J1. An elongated shaft 406 extends distally from the housing 402 and supports upper and lower jaw members 410, 412 respectively. A mechanical switch 420 is disposed on the housing 402 for controlling the operational mode of the instrument 400. The mechanical switch 420 is arranged in a proximal position to configure the instrument 400 for operation in the unilateral mode. The mechanical switch 420 controls an internal mechanism (not shown) that locks the upper jaw member 410 in a pre-set, straight position that is generally aligned with the elongated shaft 406 when the switch 420 is moved to the proximal position. The mechanical switch 420 may alternately be configured as a slider, button, lever or other appropriate actuator. In the unilateral mode, only the lower jaw member 412 is induced to pivot relative to the elongated shaft 406 (in the direction of arrows J2) in response to pivotal motion of the movable handle 404 in the direction of arrows J1. The upper jaw member 410 remains stationary relative to the elongated shaft 406 in the unilateral mode. In other embodiments (not shown) the lower jaw member 412 may remain stationary while the upper jaw member 410 pivots in a unilateral mode.

Figure 13:
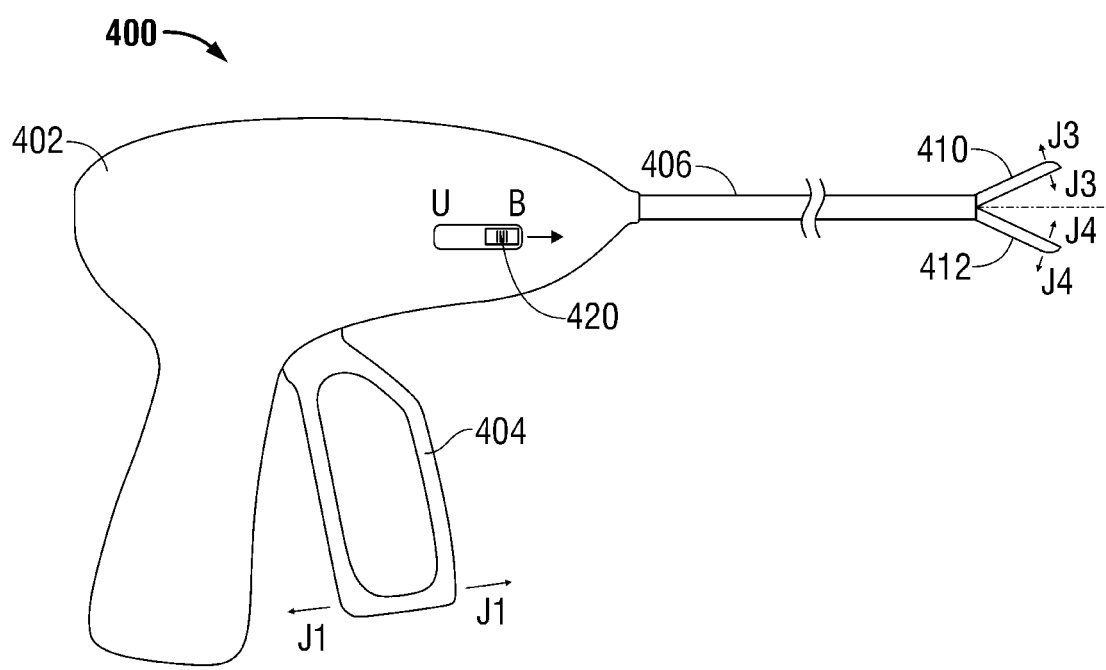
FIG. 13 is a side view of the surgical instrument of FIG. 12 arranged for operation in a bilateral mode.

The mechanical switch 420 may be moved to a distal position to configure the instrument 400 for operation in a bilateral mode as depicted in FIG. 13. When the switch 420 is moved to the distal position, the internal mechanism (not shown) releases the upper jaw member 410 from the pre-set, straight position to permit pivotal motion of upper jaw member in the direction of arrows J3. In the bilateral mode, both the upper and lower jaw members 410, 412 are induced to pivot relative to the elongated shaft 406 (in the direction of arrows J3 and J4, respectively) in response to pivotal motion of the movable handle 404 in the direction of arrows J1. In the bilateral mode, the motion of the upper and lower jaw members 410, 412 is equal and symmetrical as the jaw members 410 and 412 are opened and closed with respect to one another.

The mechanical switch 420 provides a convenient mechanism that permits a surgeon to switch between unilateral and bilateral modes during a surgical procedure. A surgeon may have a preference for one mode of operation over the other, or the type of tissue encountered and the procedure to be preformed may influence the appropriate operational mode. For example, a surgeon may find the unilateral mode more convenient when generally planar tissue is to be grasped and/or dissected. Similarly, the surgeon may find the bilateral mode more convenient for gathering large bundles of tissue or for spreading tissue apart.

The instrument 400 may be configured as a grasper, dissector, scissors, or other mechanical manipulator. The instrument 400 may also be configured for the delivery of RF (monopolar or bipolar), ultrasonic or microwave electrosurgical energy for coagulation, vessel sealing and/or ablation of tissue. Alternatively, the instrument 400 may be configured for stapling, clipping, suturing or otherwise mechanically joining tissue. Regardless of the function, the instrument 400 may be switched between the unilateral and bilateral modes during a surgical procedure such that one type of instrument, e.g., an instrument solely operational in a unilateral or bilateral mode, need not be withdrawn from a surgical site and replaced with another type of instrument to provide both unilateral and bilateral functionality.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
a housing supporting first and second actuators thereon;
a first jaw member and a second jaw member;
a first drive member defining a longitudinal axis and operatively coupled between the first actuator and the first jaw member such that manipulation of the first actuator induces pivotal movement of the first jaw member about a pivot axis, the pivot axis disposed at a non-parallel angle relative to the longitudinal axis;
a second drive member operatively coupled between the second actuator and the second jaw member such that manipulation of the second actuator induces pivotal movement of the second jaw member about the pivot axis; and a coupling member operatively associated with the first drive member and the second drive member, the coupling member selectively movable between a locked configuration and an unlocked configuration, wherein in the locked configuration the first drive member and the second drive member are coupled to one another and move concurrently to pivot the first jaw member and the second jaw member about the pivot axis in a bilateral manner, wherein the coupling member includes a peg coupled to the first drive member, and wherein the second drive member includes a plurality of holes defined therein for receiving the peg when the coupling member is moved to the locked configuration.

2. The surgical instrument according to claim 1, wherein each of the first drive member and the second drive member is coupled to a respective drive pin, and wherein each of the respective drive pins is engaged with a cam slot defined in a respective one of the first jaw member and the second jaw member.

3. The surgical instrument according to claim 2, wherein each of the cam slots defines a generally curvilinear path through the respective jaw member.

4. The surgical instrument according to claim 2, wherein each of the cam slots is disposed proximally of the pivot axis.

5. The surgical instrument according to claim 1, wherein at least one of the first drive member and the second drive member is operatively associated with an immobilization member, the immobilization member operable to selectively impede motion of at least one of the first drive member and the second drive member with respect to the housing.

6. The surgical instrument according to claim 5, wherein the immobilization member includes a peg receivable in at least one of the plurality of holes defined in the second drive member to impede motion of the second drive member with respect to the housing.

7. The surgical instrument according to claim 1, further comprising an elongated shaft extending distally from the housing and defining a longitudinal axis, wherein the first jaw member and the second jaw member are relatively movable between an open configuration wherein the first jaw member and the second jaw member are substantially spaced relative to one another, and a neutral closed configuration wherein the first jaw member and the second jaw member are closer together and generally aligned with the longitudinal axis of the elongated shaft.

8. The surgical instrument according to claim 1, wherein at least one of the first jaw member and the second jaw member includes an electrode coupled to a source of electrosurgical energy.

9. The surgical instrument according to claim 1, wherein when the coupling member is in the unlocked configuration, the first drive member and the second drive member are decoupled from one another and move independently of each other to pivot their respective jaw member about the pivot axis in a unilateral manner.

10. A surgical instrument, comprising:
a housing supporting a first actuator and a second actuator thereon;
an elongated shaft defining a longitudinal axis, the elongated shaft attached to the housing and including first and second jaw members at a distal end thereof;
first and second drive members extending through the elongated shaft, the first drive member operatively coupled between the first actuator and the first jaw member such that manipulation of the first actuator induces pivotal movement of the first jaw member about a pivot axis, the pivot axis disposed at a non-parallel angle relative to the longitudinal axis, the second drive member operatively coupled between the second actuator and the second jaw member such that manipulation of the second actuator induces pivotal movement of the second jaw member about the pivot axis;

a coupling member operatively associated with the first and second drive members; and an immobilization member operatively associated with the second drive member, the immobilization member movable between a locked configuration such that manipulation of the first actuator induces unilateral pivotal motion of the first jaw member about the pivot axis, and an unlocked configuration such that manipulation of the first actuator induces bilateral pivotal motion of both jaw members about the pivot axis, wherein when the coupling member is in the unlocked configuration, the first drive member and the second drive member are decoupled from one another and are movable independently of each other to pivot their respective jaw member about the pivot axis in a unilateral manner.

11. The surgical instrument according to claim 10, wherein the first actuator includes a movable handle pivotally supported by the housing.

12. The surgical instrument according to claim 11, wherein the movable handle is pivotable in a proximal direction to induce longitudinal translation of the first drive member in a distal direction.

13. The surgical instrument according to claim 10, wherein the first and second drive members are operatively coupled to independent first and second motors, and wherein each of the first and second drive members includes a generally flat surface disposed adjacent the generally flat surface of the other of the first and second drive members.

14. The surgical instrument according to claim 10, wherein the immobilization member includes at least one locking wing, and wherein the second drive member includes a plurality of slots, at least one slot of the plurality of slots is configured to receive the at least one locking wing therethrough.

15. The surgical instrument according to claim 10, wherein the coupling member includes a flange portion that is engaged by a biasing member, wherein the biasing member is positioned between the first drive member and the flange portion.

16. The surgical instrument according to claim 10, wherein the coupling member is selectively movable between a locked configuration and an unlocked configuration, wherein in the locked configuration the first drive member and the second drive member are coupled to one another and are movable concurrently to pivot the first jaw member and the second jaw member about the pivot axis in a bilateral manner.

17. A surgical instrument, comprising:
a housing supporting first and second actuators thereon;
a first jaw member and a second jaw member;
a first drive member defining a longitudinal axis and operatively coupled between the first actuator and the first jaw member such that manipulation of the first actuator induces pivotal movement of the first jaw member about a pivot axis, the pivot axis disposed at a non-parallel angle relative to the longitudinal axis;

a second drive member operatively coupled between the second actuator and the second jaw member such that manipulation of the second actuator induces pivotal movement of the second jaw member about the pivot axis; and a coupling member operatively associated with the first drive member and the second drive member, the coupling member selectively movable between a locked configuration and an unlocked configuration, wherein in the locked configuration the first drive member and the second drive member are coupled to one another and move concurrently to pivot the first jaw member and the second jaw member about the pivot axis in a bilateral manner, wherein when the coupling member is in the unlocked configuration, the first drive member and the second drive member are decoupled from one another and move independently of each other to pivot their respective jaw member about the pivot axis in a unilateral manner.

* * * * *